United States Patent [19]

Raymond

[11] 4,253,271
[45] Mar. 3, 1981

[54] MASS ALGAL CULTURE SYSTEM

[75] Inventor: Lawrence P. Raymond, Richland, Wash.

[73] Assignee: Battelle Memorial Institute, Richland, Wash.

[21] Appl. No.: 974,051

[22] Filed: Dec. 28, 1978

[51] Int. Cl.$^3$ ............................................. A01G 7/00
[52] U.S. Cl. ................................ 47/1.4; 47/DIG. 6; 210/221.2; 210/703
[58] Field of Search ............................ 47/1.4, 59–65; 210/44, 221 P, 3

[56] References Cited

U.S. PATENT DOCUMENTS

| | | | |
|---|---|---|---|
| 2,732,661 | 1/1956 | Spoehr et al. | 47/58 |
| 2,854,792 | 10/1958 | Juda | 47/1.4 |
| 3,155,609 | 11/1964 | Pampel | 210/3 |
| 3,218,758 | 11/1965 | Konikoff | 47/1.4 |
| 3,224,143 | 12/1965 | Tew et al. | 47/1.4 |
| 3,385,786 | 5/1968 | Klock | 47/1.4 X |
| 3,420,739 | 1/1969 | Bongers | 47/1.4 UX |
| 3,446,488 | 5/1969 | Mail et al. | 210/221 P |
| 3,468,057 | 9/1969 | Buisson et al. | 47/1.4 |
| 3,557,753 | 1/1971 | Dantoni | 119/2 |
| 3,661,262 | 5/1972 | Sanders | 210/169 |
| 3,763,824 | 10/1973 | Schoon | 47/1.4 X |
| 3,768,200 | 10/1973 | Klock | 47/1.4 |
| 3,780,471 | 12/1973 | Ort | 47/1.4 |
| 3,835,813 | 9/1974 | Katz | 47/1.4 X |
| 3,836,460 | 9/1974 | Willis et al. | 210/44 |
| 3,839,198 | 10/1974 | Shelef | 47/1.4 X |
| 3,947,359 | 3/1976 | Laurie | 210/221 P |
| 3,955,317 | 5/1976 | Gudin | 47/1.4 X |
| 3,958,364 | 5/1976 | Schenck et al. | 47/1.4 |
| 4,084,346 | 4/1978 | Stengel et al. | 47/1.4 |
| 4,085,041 | 4/1978 | Fullerton et al. | 210/44 X |
| 4,162,972 | 7/1979 | Green | 210/44 |

OTHER PUBLICATIONS

The Growth and Inorganic–Kraus et al., Plant Phys., 1954, vol. 29, pp. 205–214.
Engineering of Unconventional–Breber, 1969, Chem. Eng. Prod. Symp. Series, vol. 65, pp. 80–92.
Utilization of the Effects–Fredrickson et al., Proc. IBP/PP Tech. Mfg. Trebon, 1969, pp. 519–541.
Nutrient Transformation–Goldman et al., Journ. Envir. Eng. Div., 1975, vol. 101, pp. 351–364.
Glass Solar Collectors, Deminet, Proc. Solar Energy Fuel & Food Workshop, Univ. of Arizona, 1976, pp. 160–172.
Mass. Prod. of Algae, Goldman et al., Conf. on Biol-Solar Energy Conservation, Miami, Fla. 1976.
Photosynthesis Single Cell Protein, Protein Resources Study, Waslien, NSF/MIT 1976.
Foam Fractionation, Brunner et al., Ind. Eng. Chem. 57, 1965, pp. 40–48.
Foam Separation–Wallace et al., N.R.L. Rep. Bo. 6958, Nov. 1969.
A Continuous Recirculating–Zillioux, Marine Biol. 4, 1969, pp. 215–218.

Primary Examiner—Robert E. Bagwill
Attorney, Agent, or Firm—Klarquist, Sparkman, Campbell, Leigh, Hall & Whinston

[57] ABSTRACT

An apparatus and process for the culture of algae in a liquid medium is disclosed. The medium circulates through an open trough and is exposed to an atmosphere which is temperature regulated. The nutrient content of the liquid medium is regulated to control the chemical composition growth and reproduction characteristics of the cultured algae. Before it is allowed to strike the medium, sunlight is passed through a filter to remove wavelengths which are not photosynthetically active. Heat energy can be recovered from the filter.

15 Claims, 12 Drawing Figures

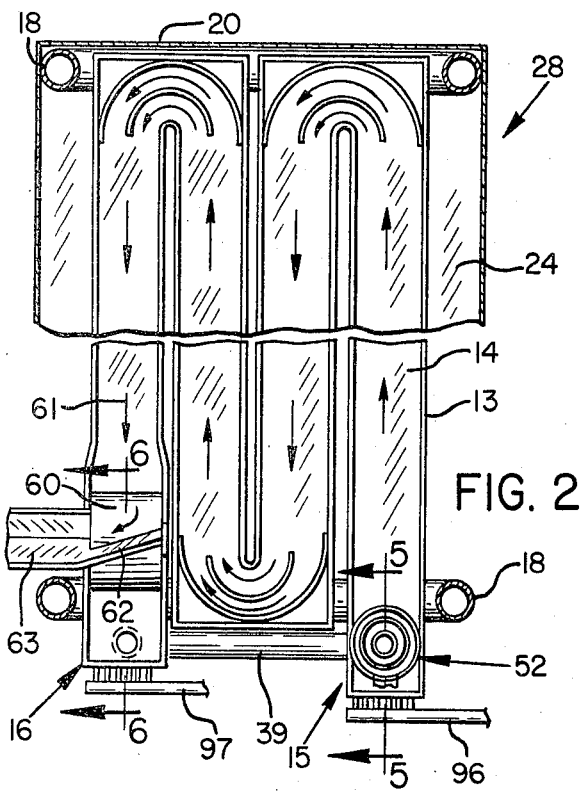

MASS ALGAL CULTURE SYSTEM

BACKGROUND OF THE INVENTION

This invention relates to a method for growing photosynthetic microorganisms in liquid suspension, and specifically to the mass culture of unicellular algae.

In recent years cultured algae has been recognized as a promising source of food and even of chemical feedstocks. As a result, a variety of apparatuses and methods have been devised to facilitate the growth of algae. High yields have been obtained in some tightly controlled laboratory experiments, but heretofore, efforts at mass algal culture have been disappointing in that they were inefficient and uneconomical.

Prior mass algal culture systems have yet to prove economical because (1) they require relatively deep containment (20-100 cm) in order to provide for temperature control; (2) they produce comparatively dilute cultures; (3) they make inefficient use of carbon dioxide and little use of infra-red radiations from sunlight; (4) they require substantial energy inputs to provide mixing to avoid thermal stratification; (5) they must process larger volumes of water to obtain the same harvest yields of algal matter that might be collectible from shallower systems; and (6) they permit little or no control and/or regulation of those environmental elements which control and regulate the performance characteristics of the cultured cells.

Further, no prior mass algal culture system has been equipped to induce and regulate the flashing-light effect efficiently. Prior apparatuses have suffered from rapid contamination by unwanted organisms and have required extensive sterilization treatments for both equipment and media. Nutrient and temperature management has not been conducted with precision in such mass culture system.

Harvesting is usually the single largest deterrent to realizing practical and economical unicellular algal production. The usual methods employed include settling, perhaps enhanced by flocculation, centrifugation, and bed evaporation. All such processes require too much time, space, and/or energy to permit reasonable commercial utility.

Even the best of existing apparatus have been operated at least than peak efficiency because currently known methods of operation are not regulated to maximize the production of cell matter.

SUMMARY OF THE INVENTION

It has now been discovered that the deficiencies of existing systems can be overcome by the use of novel apparatus and processes which permit a substantial gain in the net energy (outputs vs. inputs) obtained from the system, without being substantially more complex to operate than systems heretofore used. The mass culture apparatus disclosed can precisely regulate many variables so that the cells harvested can be controlled to be of chosen chemical compositions and produced at rates representing high and nearly constant conversion efficiencies of sunlight into stored chemical-free energy. In this way, the algal product can be chosen to meet a variety of needs.

As in some prior systems, algae is cultured in a liquid medium which flows through a shallow trough. In the present system, the trough is positioned beneath a filtering means which absorbs the infrared and ultraviolet wavelengths of sunlight passing therethrough. Algal cells in the liquid medium thus receive light of the photosynthetically active wavelengths which stimulate growth and reproduction, but are not exposed to substantial amounts of light of wavelengths which retard or are not used in those life functions. The captured wavelengths heat the filtering means which therefore functions as a solar collector. The heat energy developed can be used to control the temperature of the algal culture medium or can be converted into electrical energy for driving pump motors and other essential system components.

The algae-containing liquid medium moves through a channel or trough by gravity flow. A pump removes medium from a discharge end of the trough and redeposits it in an inlet end of the trough. A gas lift pump is uniquely advantageous for this purpose because such a pump not only circulates the liquid medium but also can be used to separate organic wastes from the medium. A stream of minute gas bubbles can be injected into the liquid medium 12 as it passes through the gas lift pump. The bubbles possess a static charge so that organic wastes in the liquid medium become attached to oppositely charged bubbles. The bubbles rise to the surface of the liquid medium carrying the electrostatically absorbed organic substances with them. When at the surface, the bubbles form a froth. This froth and the undesirable organic substances is contains, may then be easily separated from the liquid medium.

Channels of the present invention can be arranged in a serpentine pattern. Liquid medium containing growing algae is circulated through the serpentine channels at a rate sufficient to cause mixing or turbulence therein, thereby to achieve a desired periodicity of the fluid element such that its components are alternatively given access to a surface layer of the fluid and deeper layers therein. Individual algal cells, following the flow pattern of the liquid medium, are transported continuously between surface locations and regions deeper within the channels. Because the overlying algal cells are continuously and cyclically exchanged with those deeper within the medium, and because they extinguish light by absorption and scattering in direct proportion to their concentration in the medium, they progressively shade the cells to the point of virtual darkness in the deeper zones within the channels. Thus, individual cells growing within the shallow (2-5 cm deep) fluid element are exposed to alternating periods of light and darkness and exhibit the desirable growth characteristics associated with the phenomenon commonly known as the "flashing light effect" throughout most of the channel system.

Near its discharge end, the channel deepens and widens so that the cross-sectional flow area is increased. As a result, laminar flow is established within the fluid element as it approaches the discharge end.

Flow is regulated so that near stagnant conditions are produced in the surface waters at the discharge end whereby algal cells within the fluid element tend to rise to the surface, forming a thick surface film. This algal film is readily harvested either by regulating its flow over a wier or by other skim harvesting techniques. The efficiency of these techniques is improved by processes which increase the flotation of the algal cells. Such processes include (1) the electrostatic attachment of algal cells to gas bubbles within the fluid element due to the production of minute bubbles in the gas-lift pump and/or the natural formation of oxygen bubbles by the cells during photosynthesis, (2) the modification of the chemical composition of the algal cells by judicious selection and regulation of those environmental factors which direct the biosynthesis of chemical compounds less dense than the growth medium, and (3) the addition of surfactants which are less dense than water and which absorb to and increase the flotation of the algal cells.

Prior to innoculation with an algal culture, the apparatus is sterilized by preparing a liquid medium precursor containing all the acidic components of the desired liquid medium. The trough is filled with this precursor to kill any potentially contaminating organism. An alkaline substance is then added to the precursor to complete the liquid medium and raise its pH to within a range suitable for the growth of algae. The medium is innoculated with the desired algae and maintained in an environment conducive to growth and reproduction.

During operation, contamination is reduced because the channels are contained within an enclosure, in which a somewhat elevated pressure is maintained. The system is provided with means to carefully regulate nutrient and carbon dioxide content of the liquid medium and to maintain the medium within preferred temperature and pH ranges. In this way the system affords an output of algal products having more uniform and controllable chemistry, adjustable over a greater range of desirable compositions, than have heretofore been obtained in mass culture systems.

By appropriate selection of nutrient schedules it is possible to maximize cell reproduction, cell enlargement and/or the concentration of certain chemical compounds, such as lipid constituents, in the algal product. Continuous operation can be achieved by continuously or periodically adding nutrients to the medium to make up for those consumed by the growing algae and by recycling liquid medium until such time as the liquid becomes contaminated with undesirable organisms or with a toxic level of some algal secretion which can not be removed satisfactorily.

It is therefore an object of this invention to provide an algal culture system wherein algal cells are exposed to light which is chiefly comprised of photosynthetically active wavelengths and wherein algal cells are grown in shallow media (2–5 cm) and sheltered from light of wavelengths which inhibit growth and reproduction.

A further object is to provide such an algal culture system wherein filtering means absorb essentially all radiation below 350 nanometers and above 700 nanometers from incident sunlight.

It is a further object to provide a system wherein the temperature of the algal culture is regulated to provide an ideal growth environment.

An additional object is to use the nonphotosynthetic wavelengths of light to provide energy for nonphotosynthetic operations of the system.

Another object is to provide means of bringing potentially toxic dissolved organic materials into contact with gas bubbles so that they will float to the surface of a liquid culture medium where they can be conveniently removed.

An additional object is to provide a gas lift pump mechanism which both moves liquid culture medium through a trough and brings algal cells into contact with gas bubbles.

Another object is to provide a gas lift pump as aforesaid to regulate and control the build up of potentially toxic dissolved organic materials.

An object is also to provide an algal culture system wherein algal cells can be continuously grown and harvested.

Yet another object is to provide an algal culture apparatus wherein algae growing in a liquid medium are alternately exposed to periods of light and darkness to obtain the favorable growth characteristics induced by the "flashing light effect."

In addition, it is an object to provide an algal culture system as aforesaid which is of simple construction and which stores sunlight as chemical energy in excess of the amounts required for system operation.

Another object is to provide a mass culture system wherein an algal nutrient medium can be regulated to control uniformly the chemical makeup of the harvested algal product and to achieve routinely a greater productivity than has heretofore been practical.

An object is to provide a mass algal culture process capable of regulating the physiological characteristics of algae grown and reproduced therein.

It is also an object to provide a method of liquid culture medium formulation wherein a liquid precursor of the culture medium acts as a sterilizing agent for the culture growth environment.

A further object is to provide an efficient outdoor system for storing solar energy in chemical form represented by the mass culture of marine algae in a seawater based medium.

These and other objects and features of the present invention will be apparent from the drawings and description of the preferred embodiment.

BRIEF DESCRIPTION OF THE DRAWINGS

In the drawings:

FIG. 2 is a plan view of the algal culture trough and part of the associated apparatus of FIG. 1 with the walls of the enclosure and certain other parts shown in horizontal section;

FIG. 3 is an enlarged partial sectional view taken along line 3—3 of FIG. 1;

FIG. 4 is a sectional view taken along line 4—4 of FIG. 3;

FIG. 5 is an enlarged partial sectional view taken along line 5—5 of FIG. 2;

FIG. 6 is a partial sectional view taken along line 6—6 of FIG. 2 showing desired flow vectors of liquid medium approaching the outlet end of the trough.

FIG. 7 is a sectional view taken along line 7—7 of FIG. 1;

FIG. 9 is a schematic view showing the preferred sinusoidal path of a typical algae cell as it moves through an algal culture trough of the type shown in FIG. 1.

FIG. 10 is a partial plan view of an algal culture trough containing mixing riffles;

FIG. 11 is a partial sectional view taken along line 11—11 of FIG. 10; and

FIG. 12 is a schematic top view of a branched "one-pass" algal culture trough according to the present invention.

DESCRIPTION OF THE PREFERRED EMBODIMENT

Figure 1:
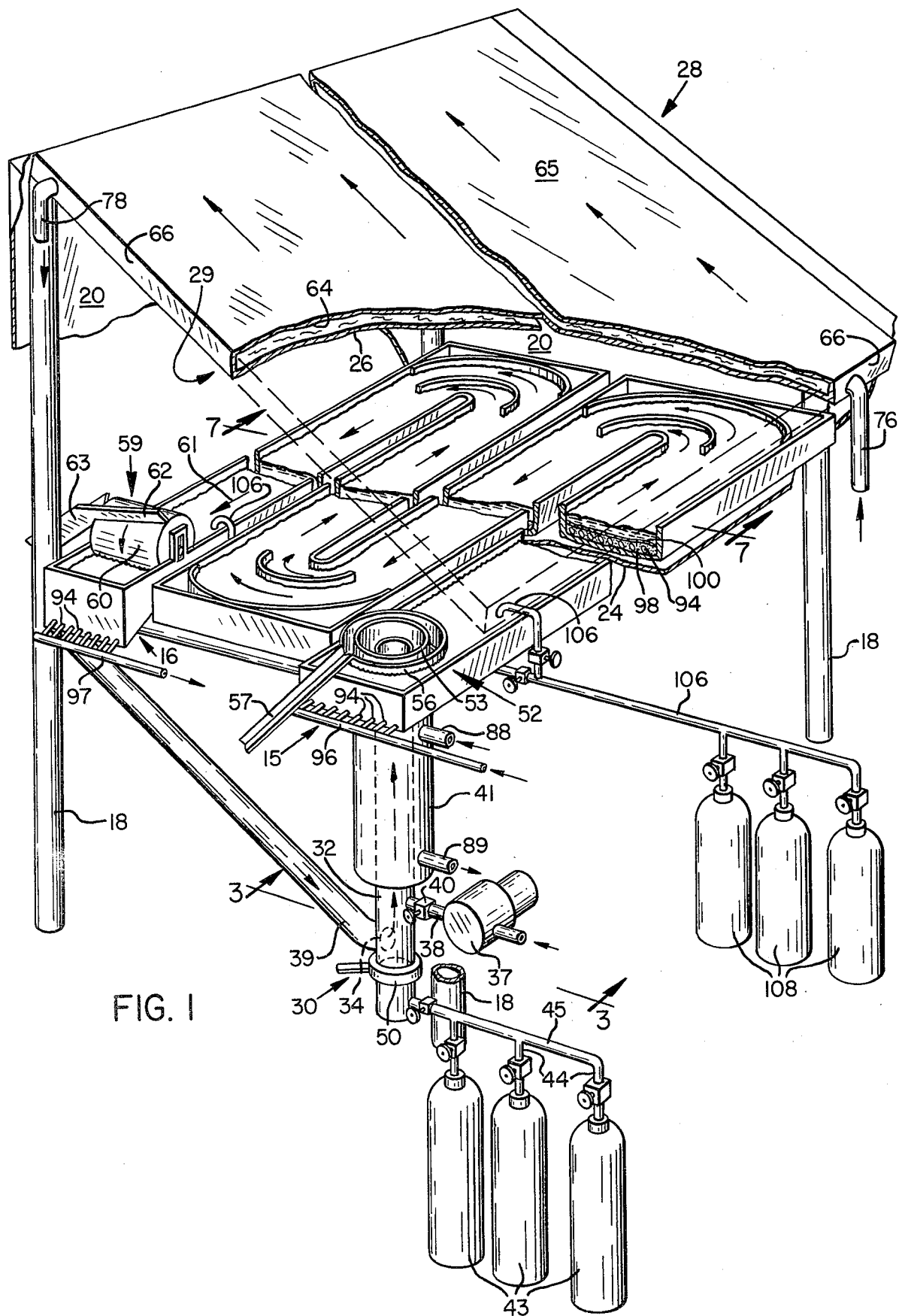
FIG. 1 is a perspective view of an algal culture system in accord with the present invention with its walls partially broken away.

The preferred apparatus for the production of algae according to the present invention is shown in FIGS. 1, 2 and 7. A trough 13 is provided to contain a liquid algae culture medium 14 in a shallow layer most preferably two to five centimeters deep. The trough has an inlet end 15 where the liquid medium is introduced and a discharge end 16 where liquid medium is withdrawn. The trough may be level or slightly inclined downwardly, e.g. at about one percent, toward the discharge end 16 to facilitate the flow of liquid medium therethrough by gravity.

Legs 18 support chamber walls 20, a floor 24 and a substantially optically transparent ceiling member 26 which together comprise an enclosure 28 for the trough 13. The enclosure defines an interior gas space 29 wherein an appropriate gaseous atmosphere may be maintained at a slightly elevated pressure so that airborne contaminants can not enter the enclosure. The walls 20 and floor 24 are preferably opaque so that incident light can enter the gas space 29 only through the ceiling member 26. With this arrangement, light and heat are the only external elements which effect the environment inside the growth apparatus.

Although nonrecirculating trough systems may be used as described below, the embodiment shown in FIGS. 1 to 7 is a recirculation system wherein the liquid medium 14 makes multiple trips through the trough 13. When the liquid medium 14 reaches the discharge end 16 of the trough, it is recirculated to the inlet end 15 by means of a suitable pump. Preferred is a gas lift pump mechanism 30 shown in FIG. 3. This pump includes a substantially vertical stand pipe 32 having a medium inlet 34 and a medium outlet 35 located above the inlet.

A stream of gas is injected into the pipe 32 through an inlet opening 36 shown in FIG. 3 as being located below the medium outlet 35. As the gas bubbles rise in the stand pipe 32, they carry liquid medium in the pipe upwardly and into the trough inlet end 15. In the illustrated embodiment, gas from a source such as an air compressor 37 or a compressed air cylinder (not shown), is delivered to the inlet 36 via a gas delivery tube 38.

The inlet 34 of the gas lift pump is connected by a recirculation pipe 39 to the discharge end 16 of the trough; and the outlet 35 of the gas lift pump is positioned to deposit liquid medium from the pump into the inlet end 14 of the trough. With this arrangement the pump 30 can be used to continuously recirculate algal culture medium through the trough 13, by withdrawing liquid from the trough's discharge end 16 and replacing it in the inlet end 15. Recirculation through line 39 is accomplished at a steady rate controlled by the rate of air addition to the pipe 32 from air compressor 37. A check valve 40 prevents the circulating culture medium from backing into the air delivery tube 38 during operation and pump downtimes.

The gas lift pump mechanism shown in FIG. 3 includes several additional features. The pump mechanism includes means for regulating liquid medium temperature throughout a wide range of temperatures between freezing and boiling. This feature is included because each species of algae develops most efficiently in a narrow range of temperatures. To maintain optimum growth temperatures the gas lift pump is equipped with jacket 41 which surrounds a portion of the piping through which the medium flows. FIG. 3 shows such a jacket surrounding the pipe 32. When the liquid culture medium 14 drops in temperature to below a desired range, a hot liquid may be circulated through the jacket 41 to elevate the temperature of the medium. Likewise, an overheated medium will give up heat to a relatively cold liquid circulating through the jacket 41. Thermostatic controls (not shown) may be provided to automatically operate this heat exchange mechanism for maximum efficiency. Heat exchange means for regulating medium temperature could, of course, be provided at other locations along the liquid medium's path as will more fully be described herebelow. Resistance heaters could also be located along the trough 13 to heat the medium.

The illustrated gas lift pump is further preferred because it includes integral means for injecting special purpose gases into the liquid medium. Although other means could be provided for this purpose, the structure of the illustrated pump mechanism 30 is unique and especially advantageous.

Gas cylinders 43 or other gas sources are each connected by a valved feeder line 44 to a special gas supply line 45. The line 45 connects to the pipe 32 at a location beneath the medium inlet 34. A porous element 47 shown in FIG. 3 is located inside the pipe 32 between the medium inlet 34 and the gas supply line 45 to disperse gas admitted through the supply line into bubbles. The illustrated element comprises upper and lower perforated plates 48, 49, each having uniform hole patterns identical to one another. Bubble size is selected by regulating the degree of pore overlap between the two adjacent plates. Pore overlap is varied by twisting a ring structure 50 to which the lower plate 49 is attached with respect to the upper plate 48 which is fixedly mounted in the pipe 32. Other contructions such as a block of microporous material, could also be used for the element 47.

Because the porous element 47 disperses gas into a stream of bubbles in the liquid medium, carbon dioxide advantageously can be added to the medium through the element. Carbon dioxide is an essential compound consumed by algae during photosynthesis; and in a mass algal culture system, it is rapidly consumed from liquid culture medium and must be replaced. Preferably, at least 235 grams of carbon dioxide should be replaced per each hundred liters of medium per day. Carbon dioxide from stack gasses, process gas or a gas production plant may conveniently be used. When the carbon dioxide is bubbled into liquid medium 14 circulating through the pipe 32, the high surface area of the bubbles and the long period of liquid contact facilitates efficient dissolution of the carbon dioxide. Carbon dioxide can thus be added to the medium at rates required to maintain a desired medium alkalinity and nitrient carbon content. Because carbon dioxide is admitted to the gas lift pump through an inlet separate from the circulating gas inlet 36, the rate of carbon dioxide addition is easily controlled independently of the liquid medium circulation rate and can be established to minimize the escape of heat-retaining carbon dioxide gas into the gas space 29.

To retain sufficient amounts of carbon dioxide in a liquid culture medium, the pH of the liquid should be maintained within an appropriate range. For fresh water media wherein carbon dioxide is retained as a dissolved gas, a pH of between 6.0 and 7.5 is preferred.

A range of 7.5 to 9.5 is best for salt water media wherein carbon dioxide is present as dissolved bicarbonate ions.

Substantially water insoluble gasses such as oxygen, hydrogen and ozone may also be delivered from one of the tanks 43 into the pipe 32. Bubbles of such gasses, produced by the porous element 47, carry a static charge which is determined by the chemical natures of the gas added through the line 45 and of the liquid medium. The static charge makes the gas bubbles attractive to oppositely charged substances in the liquid medium and the two tend to adhere to one another due to electrostatic adsorption. After the liquid medium 14 is carried from the pipe 32 into the inlet end 15 of the trough, the entrained gas bubbles tend to rise to the surface carrying with them the adhering substances.

Small, lightweight particles, such as organic waste substances tend to adhere to oppositely charged gas bubbles and to be carried to the medium surface in this manner. When bubbles carrying the organisms reach the surface, a froth tends to form on the surface of the medium 14 near the inlet end 15. By providing an appropriate foam separation device near the inlet end, the froth containing undesirable organic substances can be separated from the liquid medium.

One suitable foam separation device 52 is shown in FIGS. 1 and 5. In this device the stand pipe 32 of the gas lift pump extends upwardly through the floor of trough 13. Inside the trough, a drum 53 surrounds the pipe 32 and is provided with a liquid discharge slit orifice 54 located below the uppermost end of the pipe 32. A gate 55 is provided to regulate the fluid head inside the drum 53, by adjusting the size of the orifice 54. A collector tray 56 surrounds the top of the drum 53; and a channel flume 57 extends downwardly from the tray.

The previously described froth, which contains organic materials, collects on the surface of liquid medium inside the drum 53 as the liquid medium is continuously discharged through the orifice 54 into the trough 13. As the froth collects, it rises and eventually flows over the top of the drum into the tray 56 from which it is discharged through the flume 57.

Other devices, such as the skimming device hereinafter described, could be used for removing froth from the surface of liquid medium 14 in the trough 13.

Certain water insoluble gasses injected through the porous element 47 may also have an affinity for algal cells. If the rate of charged gas injection is sufficiently fast, bubbles of gas may adhere to cells passing through the pipe 32. Once carried into the drum 53, the algal cells tend to rise to the surface. Due to their relatively large size, the cells do not rise as rapidly as the bubbles bearing organic substances, but instead are caught up in the subsurface flow of liquid medium and carried through the orifice 54 into the trough 13.

The relative attraction of algal cells and organic substances to the gas bubbles can be regulated by selection of the types and amounts of gas injected as minute bubbles, by regulating the size of the bubbles and by adjusting the flow rate of liquid medium and the injection rate of gasses. To prevent algal cells from being removed in the foam separation device 52, the above factors may be selected to minimize algal cell flotation and maximize organic material flotation inside the drum 53.

A skimming device 59 is located in the trough 13 for continuously harvesting algal cells. One skimmer means suitable for this purpose is shown in FIGS. 1 and 6. This device comprises a porcelain drum 60 which may be lowered so that the lowermost portion of the drum extends just beneath the surface of the liquid medium 14. The drum thus provides a surface barrier without substantially impeding subsurface flow of the liquid medium. As liquid medium moves downstream in the direction of arrows 61, it passes beneath the drum 60. The drum 60 is rotated (counterclockwise in FIG. 6) so that the rising face of the drum faces upstream. As the drum rotates, floating algal cells adhere to the rising face of the drum 60 and are carried upwardly over the drum. A doctor blade or squeegee 62 is positioned against the drum 60 to scrape the algal cells from the drum surface and into a discharge chute 63. The skimming device 60 may conveniently be located in the trough 13 near the discharge end 16. It could, however, be located at any position along the trough 13.

It is advantageous to bring as many algal cells as possible to the surface of the liquid medium so that they are accessible for skim harvesting. Flotation of algal cells can be enhanced by any means capable of slowing the flow rate and reducing the mixing of liquid medium ahead of the harvester so that the pull of the liquid stream is overcome and the naturally buoyant algal cells rise to the surface. In the illustrated embodiment, flow is reduced at the discharge end 16 of the trough by regulating the rate at which liquid is removed through the pipe 39. The gas lift pump 30 is operated at a constant rate such that there is always a semistagnant buildup of medium at the discharge end 16.

The flotation of algae is further enhanced because the channel both widens and deepens as it approaches the trough's discharge end 16. This causes a laminar flow pattern to be established in the liquid medium commencing somewhat upstream of the skimmer 60. FIG. 4 shows flow vectors (represented by arrows) observed at the discharge end of the preferred channel. It can be seen that increased cross-sectional flow area causes transition from transitional and/or turbulent flow to laminar flow.

The drum 60 of the skimmer 59, acts as a gate which reduces the flow of surface liquid further so that a near-stagnant surface layer of medium is maintained upstream of the skimmer 59 as well as between the skimmer and the discharge end 16. Adjustment of the drum's skimming action regulates the discharge of surface water in the region of near stagnation.

Upstream of the discharge end 16, the liquid medium is subjected to continuous mixing as will be described hereinafter. This mixing tends to maintain algal cells in suspension. When the algal cells reach the region of laminar flow, cells are freed from the mixing action and those having densities lower than the medium tend to rise to the surface where they form a thick film in the near-stagnant surface layer. Flotation of algal cells can further be enhanced by regulating the growth environment in the trough 13 to maximize the cell's biosynthesis of chemical compounds less dense than the liquid medium 14. Surfactants less dense than the medium 14 can be added to the medium upstream of the discharge end 16. The surfactants adsorb to and increase the flotation of the algal cells.

Once on the surface, algae may be skimmed off readily by the porcelain drum 60 and constitute the end product of the system.

As an alternative to skim harvesting, surface algal cells at the discharge end 16 can be harvested from the liquid medium by a conducting regulated flow of liquid medium over an end channel weir (not shown). Control of flow over such a weir regulates the discharge of surface waters within the region of near-stagnation.

Harvesting may be accomplished most conveniently during daylight hours because algal cells emit oxygen during photosynthesis. The oxygen collects in small bubbles which cling to the algal cell wall and thus increase the flotation of the cells. Flotation is also enhanced by the minute bubbles which are formed in the airlift pump mechanism 30 and which may remain attached to the cells up to the time of harvesting.

Other devices for continuously harvesting algal cells, such as rotary screens or hydroclones, may be used. A skimmer is preferred, however, because such a device is highly efficient when used as described above.

To avoid contamination of the liquid culture medium 14 by undesirable airborne species, it is advisable that the gas space 29 be sealed from the surrounding atmosphere or be maintained at a slight positive pressure so that gas will tend to flow out of the space 29 to the surrounding atmosphere. One suitable way to avoid contamination is by continuously pumping a stream of filtered air into the space 29 and allowing any excess gas to flow out of the chamber. Some gas is, or course, added to the space from the supply lines 38, 45 via the standpipe 32. In addition, it may be helpful to inject cool, filtered air taken from the surrounding air to reduce the temperature of gas contained in the space 29. This prevents gas in the space 29 from becoming overheated which could adversely affect algal production.

To further enhance the growth of algae, this apparatus is provided with means for filtering radiation of undesired wavelengths from incident sunlight. One suitable filtering means is a shallow container of light filtering liquid 64. Such a container, as shown in FIGS. 1 and 6, may be of "sandwich" construction, including the ceiling member 26 which serves as a lower panel of the container, a spaced upper transparent panel 65 and walls 66 joining the perimeters of the two panels to define a watertight compartment. The compartment contains a layer of liquid 64 which is selected for its ability to filter undesired wavelengths from the sunlight before it enters the gas space 29. If algae is to grow properly in the system, it is necessary that the panels 26, 65 be made of a material which is substantially transparent to those wavelengths of sunlight which are photosynthetically active. Preferably the panel 65 will have a flat face inclined toward the sun at an angle of up to about 60° from horizontal to avoid reflection loss of photosynthetically active wavelengths.

A variety of different liquids might be suitable for use in the container depending upon their light absorption spectra. One especially suitable liquid is an aqueous solution of $CuSO_4$. An effective solution will contain about five to ten weight percent $CuSO_4.5H_2O$ divided by the length, in centimeters of the light's path inside the solution. Such a solution layer will trap the ultraviolet and infrared wavelengths which inhibit algal growth and/or normally would be unutilized.

A radiation absorbing gas or gel could be used in the container 62 in place of the liquid solution. A gas suitable for this purpose is a mixture of ammonia and sodium thiocyanate. Alternately, filtering can be achieved using a solid filter plate. If, for example, one of the container panels 26, 65 is impregnated with copper sulfate salt, a transparent liquid or gas could be circulated between the panels to receive heat energy absorbed from solar radiation by the impregnated panel. As a filter, the impregnated panel will suffice alone if recovery of heat energy is not desired.

Regardless of filter type, the filter should be capable of transmitting photosynthetically active wavelengths and at the same time absorbing or reflecting at least ninety-nine percent of all incident radiation below 350 nanometers and above 700 nonometers.

Because the air in the gas space 29 will begin to receive excessive heat during daylight hours from the filter if the filter's temperature increases to an undesirably high level, a pane of transparent material (not shown) can be placed a small distance beneath the ceiling member 26 to form a compartment. A layer of air trapped in such a compartment would thermally insulate the air space 29 from the filter. Cool air could be circulated through such a compartment to further prevent the transfer of heat from the filter into the air space 29.

Figure 8:
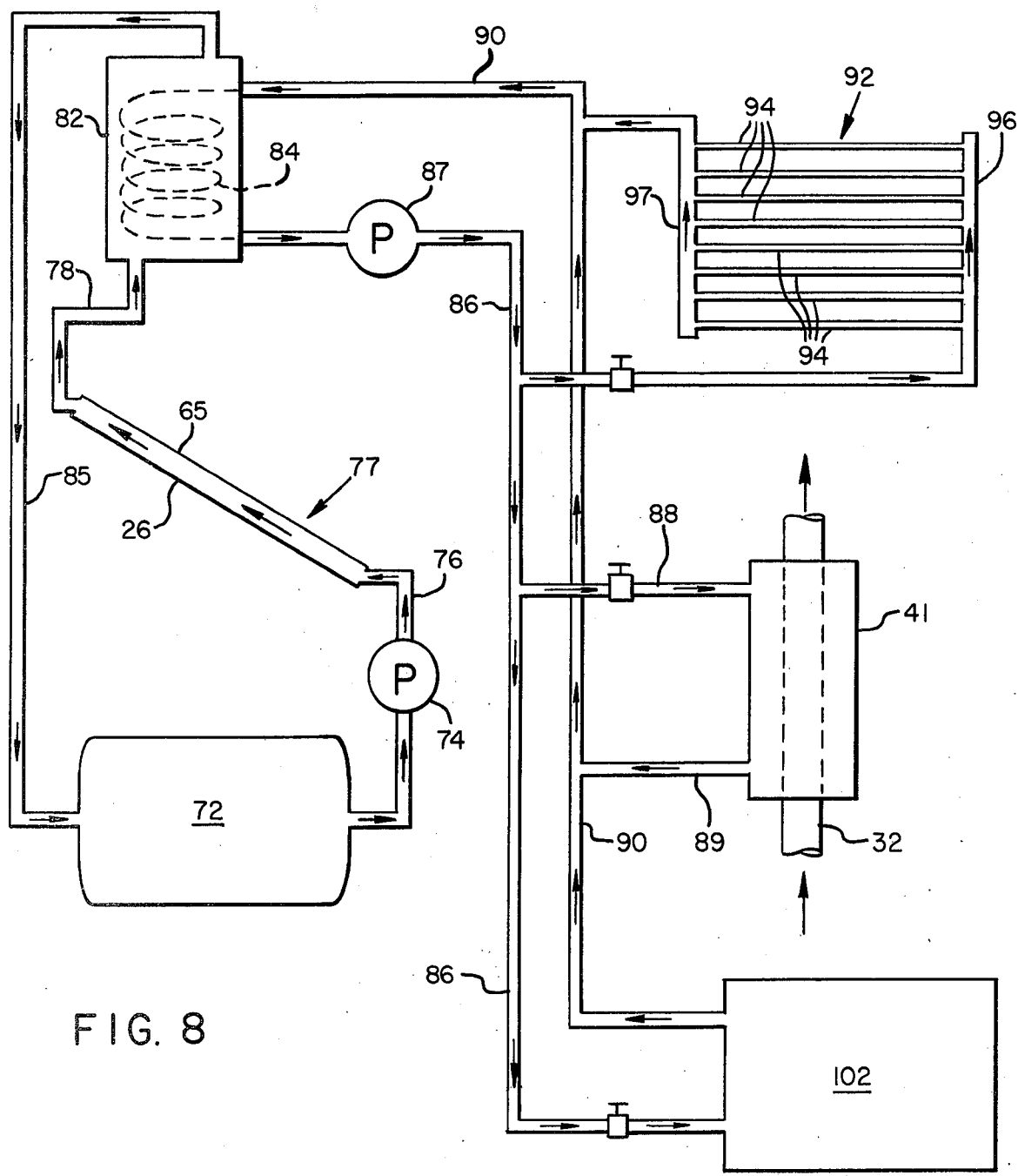
FIG. 8 is a schematic diagram of the algal culture system's solar heat recovery system.

When using a liquid solution as a filtering medium, heat can be removed directly from the liquid 64 to prevent overheating inside the air space 29. FIG. 8 shows schematically a heat exchange system both for controlling the temperature of liquid 64 and for utilizing heat energy collected in the liquid. A supply of the liquid 64 is maintained in a reservoir 72. A stream of the relatively cool liquid in the reservoir 72 is pumped by pump 74 through a distribution tube 76 and into the compartment between the panels 26, 65 of a "sandwich-type" solar collector 77 as described above. Preferably, the tube 76 connects at the lowermost part of the compartment so that liquid 64 is injected along the lowest sidewall of the container, but other flow patterns could be used.

As the pump 74 continues to operate, the injected liquid flows upwardly between the panels 26, 65 collecting heat. The heated liquid flows out of the upper end of the compartment through a tube 78 which is connected to a heat exchange unit 82. Inside the unit 82, excess heat is removed from the stream of filtering liquid by indirect heat exchange with a cooling fluid, preferably water, or some other non-toxic fluid having a high heat capacity. The fluid is circulated through a heat exchange coil 84 whereby it receives heat energy from the liquid 64. The temperature or the cooling liquid is preferably thermostatically controlled to maintain the filtering liquid at a decreased temperature. After it is cooled in the heat exchange unit 82, the filtering liquid 64 is returned to the reservoir 72 through a return tube 85. If heating of the liquid 64 is required at any time, a heated fluid can be circulated through the coil 84.

Heat energy recovered in the exchange unit 82 can be used in other process applications, stored for heating use during cold periods or, if of sufficient quantity and quality, converted into electrical energy. The heat cooling fluid can be pumped from the heat exchange unit 82 into a distribution line 86 by a pump 87. The distribution line connects to an inlet pipe 88 of the previously described jacket 41. An outlet pipe 89 returns cooled fluid to the heat exchange unit via a collection line 90.

Another device which can utilize the heat in the cooling fluid is a trough heating system 92. The system includes temperature control lines 94 which are connected between an input manifold 96 and an output manifold 97. As best shown in FIGS. 1 and 7, the lines 94 are embedded in a layer of sand or similar material 98 in the bottom of the trough 13. A layer of flexible sheeting 100, e.g. of polyvinyl chloride or butyl rubber, covers the sand 98 and comprises the floor of the channel defined by the trough 13. When the temperature of liquid medium 14 in the trough 13 descends below a desired level, fluid heated in the heat exchange unit 82 can be diverted through the input manifold 96 into the temperature control lines 94. Heat from the fluid thus defuses into the sand 98 to warm liquid medium 14 in the trough 13. The fluid is returned to the collection line 90 via the output manifold 97.

Heated fluid can be diverted to other process apparatus, represented schematically in FIG. 8 as a box 102. Such apparatus might include means for converting heat energy into electricity for powering pumps and other equipment.

The apparatus of the present invention further includes a device to induce mixing of the liquid medium 14 as it passes through the trough 13. The illustrated embodiment includes a serpentine trough having a series of curves positioned at intervals. Liquid medium is circulated through the trough at a rate sufficient to induce controlled mixing therein. As a result vertical eddies are induced and the liquid medium follows a vortical path. In this mixing pattern algal cells periodically move between surface layers of the medium and layers near the bottom thereof. Periodic mixing in turn reduces settling and early floatation of algal cells.

Periodic or continuous medium mixing is further useful because plants grow most effeciently when subject to alternating periods of light and relative darkness. Because algal cells extinguish light by absorption and scattering in direct proportion to their concentration in the medium, relatively little sunlight penetrates to the deepest portion of the liquid medium 14 as compared to the amount of light available just below the surface. The above described periodic mixing thus causes algal cells to move alternately between well lighted positions (adjacent to the surface) and shaded areas (distant from the surface). This in turn causes the cells to exhibit the desirable growth characteristics associated with the phenomenon commonly known as the "flashing light effect." Preferably, the trough 13 is designed to produce periodic culture mixing such that individual algal cells follow a substantially sinusoidal path, as shown by the arrows in FIG. 9, during their travel from the inlet end 15 to the discharge end 16.

To obtain the most efficient use of available sunlight, the trough system should contain the liquid medium in a relatively thin layer, between about 0.5 and 5.0 centimeters in depth and more preferably between 2.0 and 5.0 centimeters. Maintaining such a shallow layer facilitates culture mixing for the purpose of inducing the "flashing light effect" phenomenon.

When operating a recirculating system with liquid medium in a 0.5 to 5.0 centimeter depth range, the "flashing light effect" is maximized if the algal culture density is maintained so that at all depths, light intensity is extinguished between one hundred and one thousand fold multiplied by the liquid medium depth in centimeters. In other words, the culture density will be in the most proficient range if light intensity at a given depth multipled by the depth in centimeters gives a figure between about 0.1 and 1.0 percent of the light intensity at the surface of the liquid medium.

If a portion of the algal culture is not recirculated with the liquid medium, culture density at the inlet end of the trough may be at a density below the above specified amount. The proscribed culture density should, however, be reached at some point along the trough so that algal growth thereafter will be progressively enhanced by optimum "flashing light" conditions.

While the serpentine trough of the illustrated device is quite suitable for moving cells in a vortical path, other options are available. It might, for example, prove desirable to culture algae in a long straight trough. Appropriate mixing will automatically result if a suitable liquid flow rate is maintained. Mixing can further be created by positioning baffles or other mixing devices at spaced intervals in a trough. Such devices can provide the turbulence necessary to obtain a mixing pattern of the type illustrated by arrows in FIG. 9. Other techniques well known in the art can be applied to generate the desired turbulences.

One especially suitable mixing device is a cylindrical riffle 104 as illustrated in FIGS. 10 and 11. Such riffles may be located at intervals along the trough's channel bottom to create turbulence and thus culture mixing in the flowing liquid culture medium 14. The greatest amount of turbulence occurs just downstream of a riffle and recedes thereafter. Riffle spacing should thus be set so that a riffle is located at each point where turbulence induced by the immediately proceeding riffle has died down.

To make up for nutrients which are consumed by the algae during their growth and to regulate the pH of the nutrient medium, the apparatus of the present invention includes lines 106 shown in FIG. 1 as extending from a plurality of tanks 108 containing solutions of make up nutrients and/or liquids for adjusting the pH of the liquid medium 14. Make up nutrients from the tanks are pumped into the trough 13 via the lines 106 to replenish the liquid medium 14. A plurality of such nutrient make up and/or pH adjustment lines may be positioned at intervals along the trough to add nutrients or liquids to adjust pH wherever needed. The lines can also by used to add water to the trough 13 to make up for losses due to evaporation and to add carbon dioxide to the liquid medium. Periodic sampling and testing of the liquid medium can be used to determine the amount of nutrients, pH and salinity adjusting materials, carbon dioxide or water to be added through each nutrient make up line 106. A variety of alternative means for monitoring and replenishing the nutrient medium 14 will be apparent to one skilled in the art.

By careful regulation of the nutrient medium, it is possible to uniformly control the quality and chemical composition of the ultimate algal product. This is because algal cells of a single species are found to have physiological characteristics which differ depending upon the environment in which they are cultured. Factors affecting the algae include light wavelength and exposure timing, chemical composition of the nutrient, concentration of cells in the culture, and temperature. Each such factor is carefully controlled by the above described system.

It has been found, for example, that maximum lipid production can be achieved if the nitrogen concentration of a culture medium is reduced when the culture approaches its maximum cell population. Thus, by regulating the nutrient medium it is possible to control the lipid content of the product algae.

OPERATION

The basic operation of the present invention will be apparent from the forgoing description of the apparatus. The trough 13 is filled with liquid culture medium and innoculated with algae. The airlift pump 30 is activated by introducing gas through the line 40. This causes the liquid medium, containing rapidly growing algal cells to circulate through the channels as a shallow layer overlying the flexible sheeting 100. The flow rate is selected to induce the desired mixing of liquid as it flows through the channels.

While the system operates, the thermostatically controlled heat exchanger 82 maintains the temperature of the filtering liquid 64 at a desired level. Also, a fluid at an appropriate temperature is circulated through the jacket 41 and/or temperature control lines 94 to maintain the liquid medium within an efficient operating temperature range. Carbon dioxide is continuously fed to the liquid medium 14 through the line 45 of the gas lift pump mechanism and/or the lines 106. After an initial operating period, samples of the nutrient material are taken and, if the samples indicate that the nutrient level has dropped below a desired minimum, makeup nutrients are added through line 82 to promote further algal reproduction and/or cell growth. Once the algae has reproduced to a desirable concentration and cell size, the harvesting mechanism 59 is lowered into the liquid 14 and the drum 60 activated to commence harvesting.

The continuous growth of high-lipid algal cells in recirculating liquid medium can be accomplished by establishing coordinated harvesting and nutrient addition schedules as follows. The culture is established in a full strength liquid culture medium. As the culture grows, nutrients are added periodically to maintain their concentrations within their desirable range. When the rate of cell reproduction reduces as the cell concentration approaches its limit, as determined by an electronic particulate cell counter or similar device, nitrogen compounds are eliminated from the makeup nutrients until the nitrogen content of the liquid medium drops to about fifty percent of the amount initially present in the complete medium. Subsequent nutrient additions are adjusted to maintain nitrogen at the fifty percent level while other nutrients are at full strength.

After a period at these conditions, total cell mass of the culture will have increased, especially the lipid content thereof. Harvesting is then commenced until about fifty percent of the cells are separated from the liquid medium. Once this has been done harvesting is stopped, the nitrogen content returned to full strength and the entire process repeated.

It is desirable that both the trough 13 and the liquid medium 14 be sterilized before use. This is especially true where natural seawater is a component of the liquid medium. If such a preliminary step is not taken, the liquid medium may be contaminated with undesirable organisms. The present system provides a unique method of self-sterilization as will be apparent from the following example.

EXAMPLE

A culture of *Phaeodactylum tricornutum* was grown in an apparatus of the type previously described. This particular marine algae was selected because of its unique growth characteristics and usefulness as an end product. It is further advantageous for cultivation because it has been observed to secrete substances having antibiotic activity. Such secretions may inhibit the growth of bacteria in the liquid nutrient medium. Because *Phaeodactylum tricornutum* does not require external supplies of silica or vitamins, these nutrients can be excluded from the liquid medium to inhibit the growth of contaminating micro-organisms requiring these nutrients.

A variety of liquid mediums might be used successfully, for the culture of *Phaeodactylum tricornutum*, but exceptional results are achieved using a medium which includes sea water in which is dissolved a mixture of nutrient salts which, in grams per 100 liters of sea water, comprises 38.0—63.4 g. $HNO_3$, 5.9—9.8 g. $H_3PO_4$, 3.2–5.4 g. KCl, 1.40–2.33 g. $Na_2EDTA$ (ethylene diaminetetraacetic acid disodium salt), 0.015–0.025 g. $FeCl_3 6H_2O$, 0.00275–0.00460 g. $(NH_4)_6Mo_7O_{24}.4H_2O$, 0.0008–0.0013 g. $H_3BO_3$, 0.00030–0.00050 g. $ZuCl_2$, and lesser amounts of both $CuCl_2.2H_2O$ and $MnCl_2.4H_2O$, and an amount of KOH sufficient to raise the pH of said solution to within the range of 7.6–7.8.

An experimental liquid nutrient medium was accordingly prepared from 100 liters of sea water and 50.7 g. $HNO_3$, 7.8 g. $H_3PO_4$, 4.3 g. KCl, 1.86 g. $Na_2EDTA$, 0.020 g. $FeCl_3.6H_2O$, 0.00368 g. $(NH_4)_6Mo_7O_{24}.4H_2O$, 0.00105 g. $H_3BO_3$, 0.00040 g. $ZnCl_2$, lesser amounts of both $CuCl_2.2H_2O$ and $MnCl_2.4H_2O$, and an amount of KOH sufficient to raise the pH of the nutrient medium to within the range of 7.6–7.8. All of the above ingredients except the KOH were combined to form a liquid nutrient medium precursor which was introduced into the trough 13 and pipes 32, 39 of the apparatus. Due to its nutrient content, the precursor was substantially acidic (pH 2.2) so that potentially contaminating organisms in the sea water, trough and pipes were killed by a period of exposure to the acidity of the precursor.

At the completion of this sterilization step, the KOH was added to the precursor to bring the precursor to a pH suitable for growth of the *Phaeodactylum tricornutum*, to complete the nutrient content of the liquid nutrient medium and to bring the level of liquid medium in the trough up to an average running depth of 2.2 centimeters. The pH range of 7.6–7.8 was well within the pH range of 7.5 to 9.5 preferred for maintaining a substantial bicarbonate concentration in the sea water based medium. The medium was circulated by the gas lift pump for a period sufficient to completely mix the ingredients. Thereafter the completed medium 14 was innoculated with a culture of the algae. Artificially formulated sea water could have been used in place of natural sea water to reduce the need for sterilization steps, but it is almost impossible to formulate sea water accurately.

The trough was located beneath a transparently bottomed tray containing a three centimeter layer of an aqueous solution containing three weight percent copper sulfate. Using this filter nearly ninety percent of infrared radiation was removed from incident sunlight.

The innoculated liquid medium was continuously circulated at a mean flow rate of one foot per second. The algae were allowed to grow and reproduce and did so rapidly. Nutrients were replenished as needed. After a period of rapid reproduction, cell division rate decreased, indicating that a near maximum cell concentration in the light had been reached. Thereafter, the liquid medium and entrained algae were further circulated and nutrients added as needed to maintain cell metabolism, but no $HNO_3$ was added with the makeup nutrients. The nitrogen content of the medium was thus allowed to become substantially depleted. In this nitrogen-lean medium, algal cells continued to grow in size and weight, but cell division rate was greatly reduced. The amount of cell matter continued to increase and the lipid content of the cells increased markedly. Most efficient lipid production resulted when the liquid medium was maintained in the temperature range between 22° and 34° C.

When the concentration of algae reached approximately four grams per liter of liquid medium, about half the algae was harvested leaving about two grams of algae per liter of medium. Makeup nutrients and water were added to the remaining liquid medium to bring its volume and nutrient content, including nitrogen, back up to the full strength. Cell division, growth and harvesting proceeded continuously according to the steps previously described.

During the entire growth period, a temperature condition was maintained to enhance the growth and reproduction of algal cells. Temperature in the airspace 29 was maintained at a maximum of 30° C. by circulating cooled, filtered air through the space on warm days. The temperature of the liquid medium 14 was maintained between 18° and 28° C. with the highest temperatures occurring during daylight hours and the lowest temperatures at night. Average medium temperature during the experimental period was 24° C.

Operating in this manner a *Phaeodactylum tricornutum* production rate significantly higher than has previously been reported for mass culture systems was achieved. The presence of KOH in the liquid medium appeared to cause a change in the algal cell morphalogy and to cause an increase in the cells' nutrient intake. Nitrogen intake by the cells was extremely rapid considering that the medium contained nitrogen as nitrate ions.

The source culture used to innoculate the liquid medium 14 was typical of commonly described *Phaeodactylum tricornutum* cultures and contained the typical ovate forms. However, following exposure to the nutrient medium described, the ovate forms disappeared, leaving only the fusiform type. In this medium, the fusiform cells enlarged greatly, attaining forty microns in cases, and the entire cell volume filled to the extent that extension arms (normally present) were absent. Cells grown under these conditions contained nearly four times the cytoplasm mass of normal fusiform cells and thus were producing nearly four times the weight for each parent cell division.

Furthermore, the cells showed an entirely new mode of cell division possibly due to the high concentration of potassium ions in the liquid medium. Large fusiform cells were observed having one or more buds gradually protruding near the apex. These buds continued to expand outwardly until an equivalent number of legs would form. Indentation of the cell would continue until there were two or more cells, still connected apically. It was not uncommon to see three and four cell clusters radiating outward from the center where they would remain connected. It thus appears that *Phaeodactylum tricornutum* may have the capacity to produce three to four cells per cell division in a properly selected liquid medium.

It was further observed that the normal sequence for cell enlargement during night hours and cell division during daylight hours was reversed during this experiment.

From the harvest results obtained in this experiment, it can be extrapolated that a yield of 38.06 ash free dry tons of algae per acre-year would be obtained when using the system described. Assuming further optimization, yields of seventy to ninety tons seem within reach for certain locations and climatic conditions. The experimental results are far superior to those previously reported and indicate a photosynthetically active radiation utilization efficiency rate far above the values achieved by previous mass algal culture systems.

By the method of operation described in the above example, a liquid medium can be continuously recycled and reused until such time as it becomes contaminated with undesired organisms or until waste substances which cannot be removed from the liquid medium accumulate to a toxic level.

The apparatus described can be used to culture both fresh water and marine algae. Although *Phaeodactylum tricornutum* is an especially suitable marine species for mass culture, numerous other species could be reproduced by means of the present invention. Examples of such species appear in the following non-exclusive list:

I. MARINE/ESTUARINE TYPES

*Fragilaria sublinearis*
*Skeletonema costatum*
*Cyclotella nana*
*Isochrysis galbana*
*Pavlova gyrens*
*Monochrysis lutheri*
*Coccolithus huxleyi*
*Nitzschia palea*
*Dunaliella tertiolecta*
*Prymnesium paruum*

II. FRESHWATER TYPES

*Chlorella spp.*
*Chlamydomonas reinhardtii*
*Synedra acus*
*Scenedesmus spp.*
*Asterionella formosa*
*Navicula spp.*
*Nitzschia spp.*
*Fragilaria spp.*
*Chrysococcus spp.*
*Cyclotella spp.*
*Dinobryon spp.*

Freshwater algae may be easier to maintain in a continuous process than marine algae because media suitable for marine algae are based on seawater which contains a very complex mixture of nutrients, many of which are present in minute concentrations. It is more difficult to monitor and maintain the chemistry of seawater based media as opposed to media based on freshwater.

While I have shown and described a preferred embodiment of my invention, it will be apparent to those skilled in the art that changes and modifications may be made without departing from my invention in its broader aspects.

For example, troughs for containing the nutrient medium can be substantially straight and can be constructed to sufficient length so that algae would grow to their maximum concentration and size during one trip through the trough. Nutrients can be injected at intervals along such a trough to maintain a desired nutrient content. Heat exchange means can be provided at intervals along the trough to regulate the temperature of the liquid medium.

Such a "one-pass" trough can be used to provide multiple crops, by withdrawing a portion, e.g. fifty prcent, of the liquid medium containing a mature culture and replacing the withdrawn portion with fresh nutrient medium prior to the terminus of the trough.

This can be repeated at intervals along the trough at any location where the culture reaches a desired state of maturity. The makeup nutrient medium can be changed at each such location, as desired, so that different portions of the trough will produce algal cells having different characteristics.

Another means for obtaining cells of different characteristics from a "one-pass" trough would be to branch the trough as shown schematically in FIG. 12. Instead of adding makeup medium as described above, each branch line can e reduced in size so that it carries only a portion of the total culture. The trough 110 of FIG. 12 has an inlet end 114 and three discharge ends 116, 118, 120. As liquid medium flows through the trough it is divided into separate streams by longitudinal baffles 122. Because the different branches are of different lengths, the maturity of the culture removed depends on the total channel length between the inlet end and a particular discharge end. Algal cells may have different characteristics depending upon the maturity of the culture so that algae harvested from the various branches may be best suited for differeing uses.

When culturing *Phaeodactylum tricornutum*, for example, cells removed at the discharge end 116 might best be used as a protein source. Depending on the branch spacing, cells taken from the discharge end 118 might be most useful as a source of lipids and those which complete the journey to discharge end 120 best used for the production of antibiotics. Careful regulation of nutrient conditions in each of the separate channels could further enchance the variation among algal cells.

What is claimed is:

1. A gas lift pump mechanism for circulating a liquid medium containing an algal culture and for facilitating the separation of suspended substances from said liquid medium comprising:
   a substantially vertical stand pipe having a liquid medium inlet and a medium outlet located above said inlet;
   first gas inlet means for introducing a sufficient volume of gas into liquid medium inside said pipe to cause said medium to rise therein; and
   second gas inlet means, separate from said first gas inlet means, for introducing a stream of minute gas bubbles into said liquid medium inside said pipe which bubbles adhere to suspended substances in said liquid medium and increase the buoyancy of said substances.

2. The pump mechanism of claim 1 further comprising heat exchange means associated with said vertical stand pipe to adjust the temperature of liquid medium as it moves through said pipe.

3. The pump mechanism of claim 1 wherein said first and second gas inlet means are located at different elevations inside said stand pipe.

4. The pump mechanism of claim 3 wherein said first gas inlet means is located above said second gas inlet means.

5. The pump mechanism of claim 1 further comprising:
   means for supplying a stream of air to said first gas inlet means and
   means for supplying a stream of $CO_2$ to said second gas inlet means.

6. A process for separately removing impurity substances and suspended algal cells from a continuously recirculating liquid algal culture medium which contains said impurity substances and said cells, said process comprising:
   bringing algal cells and impurity substances carried in a continuously recirculating liquid medium into contact with gas bubbles to increase the buoyancy of said cells and of said impurity substances;
   moving said liquid medium through a trough at such a rate that the gas bubbles carry relatively small and light impurity substances to the surface of said medium and that said algal cells, which are relatively large and heavier, and which have adsorbed said gas bubbles but are carried downstream by the current and do not rise to said surface;
   removing said light impurity substances from said surface at a first location along said trough;
   at a second location downstream of said first location, reducing the rate at which said liquid medium moves through said trough so that algal cells with adsorbed gas bubbles rise to said surface at said second location; and
   removing a fraction of the algal cells circulating in said medium from said surface at said second location.

7. The process of claim 6 wherein the impurity substances comprise dissolved organic substances which, when contacted with gas bubbles, form a foam that rises to the surface of the medium.

8. A system for mass culture of algae comprising:
   a trough defining a channel which is substantially horizontal;
   circulation means for moving a flow of an aqueous nutrient medium innoculated with unicellular algae through said channel from one end thereof to the other comprising a gas lift pump having a substantially vertical stand pipe with a medium inlet, a medium outlet located above said inlet and means for introducing a sufficient volume of gas into the aqueous medium inside said stand pipe to cause said medium to rise therein;
   said outlet comprising means for separating froth from said medium, delivering said medium to said channel and discharging said froth;
   gas-liquid contact means within said gas lift, and separate from said aforementioned means for introducing gas, for bringing algal cells in said medium into contact with minute bubbles containing a substantial proportion of carbon dioxide which bubbles adhere to said cells causing them to rise to the surface of said medium in said trough;
   harvesting means for removing said cells from said surface, said harvesting means being located in said trough downstream of said gas lift pump; and
   discharge means for said medium connected to said channel downstream of said harvesting means.

9. A system as defined in claim 8 and comprising means for reducing the rate of flow of said medium adjacent said harvesting means to facilitate rise of said algal cells.

10. A system as defiend in claim 8 wherein said harvesting means is located at the opposite end of said trough from said gas lift.

11. A system as defined in claim 10 wherein said discharge means for said medium is connected to said inlet of said gas lift to recirculate said medium.

12. A system for mass culture of microalgae comprising:
    a trough having inlet and discharge ends;

an aqueous medium precursor in said trough, said medium precursor comprising sea water in which is dissolved a mixture of nutrient salts which consist essentially of $HNO_3$, $H_3PO_4$, $KCl$, $Na_2EDTA$, and trace amounts of $FeCl_3.6H_2O$, $(NH_4)_6Mo_7O_{24}.4H_2O$, $H_3BO_3$, $ZnCl_2$, $CuCl_2.2H_2O$ and $MnCl_2.4H_2O$;

an amount of KOH sufficient to adjust the pH of said solution to within a range which facilitates a desired reproduction and growth pattern for a selected algal species and to complete an aqueous medium suitable for the culture of said algal species and to fill said trough to a shallow depth;

walls defining an enclosed gas space above the surface of said aqueous medium precursor;

a gas lift pump to circulate said liquid medium through said trough, said pump comprising a substantially vertical stand pipe having a medium inlet, a medium outlet located above said inlet and means for introducing sufficient gas into aqueous medium inside said pipe to cause said medium to rise therein and separate means for introducing minute gas bubbles comprising substantial amount of carbon dioxide into aqueous medium inside said pipe to increase the buoyancy of organic substances and of microalgae in said medium by adsorption of said minute gas bubbles, said inlet and outlet being connected to said trough at locations adjacent said discharge and inlet ends respectively so that circulation of said medium in said trough from said inlet end toward said discharge end is facilitated;

a source of carbon dioxide;

tubing means connected between said means for injecting a stream of minute bubbles and said source of carbon dioxide, for directing a flow of carbon dioxide from said source into said liquid medium;

skimming means for skimming off organic substances raised to the surface of said medium due to adsorption onto minute bubbles in said stand pipe;

harvesting means for skimming off microalgae raised to the surface of said medium;

a container comprising two substantially transparent panels which are closely spaced and joined together to define a water-tight compartment therebetween, said container being positioned such that sunlight passes through said panels and subsequently strikes said medium circulating through said trough;

an aqueous $CuSO_4$ solution contained in said compartment to serve as a filter which adsorbs infrared and ultraviolet radiation of said light;

mixing means for causing said medium to travel through said trough in a turbulent manner so that individual algal cells are alternately positioned in portions of said medium distant and adjacent to said light source and thus are alternately exposed to maximum intensity light when in said adjacent portion and decreasing light intensity at progressively more distant portions;

means for maintaining the temperature of said aqueous medium within a range conducive to the growth and reproduction of said algal species;

means for extracting heat energy from said $CuSO_4$ solution; and means for replenishing nutrient salts in said medium as they are consumed by said microalgae so that sufficient nutrients are maintained to sustain desired algal growth and reproduction rates.

13. A continuous process for mass culture of a selected species of marine microalgae comprising:

filling an algal culture container with a liquid culture medium precursor comprising sea water in which is dissolved a mixture of nutrient salts which consists essentially of $HNO_3$, $H_3PO_4$, $KCl$, $Na_2EDTA$, and trace amounts of $FeCl_3.6H_2O$, $(NH_4)_6Mo_7O_{24}.4H_2O$, $H_3BO_3$, $ZnCl_2$, $CuCl_2.2H_2O$ and $MnCl_2.4H_2O$;

adding an amount of KOH to said precursor sufficient to adjust its pH to a level which facilitates a desired reproduction and growth pattern for a selected algal species and to complete said precursor's nutrient content whereby a liquid medium suitable for the growth of said algal species is formed;

innoculating said medium with a culture of said algal species;

circulating said innoculated medium through an open trough of shallow depth by withdrawing medium from one end of the trough and replacing it in the other end;

maintaining the temperature of said innoculated medium within a range conducive to the growth and reproduction of said algal species;

channeling the flow of innoculated medium from said one end of said trough through the vertical stand pipe of a gas lift pump mechanism equipped for the introduction of minute gas bubbles comprising substantial amounts of carbon dioxide into liquid medium passing therethrough to:

a. accomplish said circulating; and b. bring organic substances and the cells of said algal culture into contact with a stream of minute gas bubbles which are adsorbed thereon to increase the buoyancy of said organic substances and said microalgae so that they tend to rise to the surface of medium in the trough;

moving liquid medium containing dissolved organic substances and algal cells with adsorbed minute gas bubbles through said trough at a rate such that the relatively small and light organic substances with adsorbed gas bubbles rise to the surface of said medium and the relatively large and heavier algal cells with adsorbed gas bubbles are carried by the current and not allowed to rise to said surface;

skimming said organic substances from said surface;

subsequently slowing the rate at which said liquid medium moves through said trough so that algal cells with adsorbed gas bubbles rise to said surface;

skimming algal cells from said surface;

exposing the surface of medium in the trough to sunlight which has been filtered sufficiently to facilitate the photosynthesis of the microalgae by removing light wavelengths which inhibit algal growth and reproduction, while transmitting photosynthetically active wavelengths;

alternately positioning individual cells of the algae in portions of said medium distant and adjacent to said medium surface and thus alternately exposing the cells to maximum light intensity when adjacent to said surface and decreasing light intensity when progressively more distant from said surface;

replenishing nutrient salts in the medium as they are consumed by said microalgae so that sufficient nutrients are maintained in said medium to sustain desired algal growth and reproduction rates; and injecting $CO_2$ into said medium in sufficient quantity to maintain a desired alkalinity and nutrient carbon content in said medium.

14. A system for mass culture of marine microalgae comprising:
a trough having inlet and discharge ends;
an aqueous medium precursor in said trough, said medium precursor comprising sea water in which is dissolved a mixture of nutrient salts which, in grams per 100 liters of sea water, consist essentially of 50.7 g. $HNO_3$ 7.8 g. $H_3PO_4$, 4.3 g. KCl, 1.86 g. $Na_2EDTA$, 0.020 g. $FeCl_3.6H_2O$, 0.00368 g. $(NH_4)_6Mo_7O_{24}.4H_2O$, 0.00105 g. $H_3BO_3$, 0.00040 g. $ZnCl_2$, and lesser amounts of both $CuCl_2.2H_2O$ and $MnCl_2.4H_2O$;
an amount of KOH sufficient to adjust the pH of said solution to within a range which facilitates a desired reproduction and growth pattern for a selected marine algal species and to complete an aqueous medium suitable for the culture of said algal species and to fill said trough to an average running depth between 0.5 and 5.0 cm.;
walls defining an enclosed gas space above the surface of said aqueous medium precursor;
a gas lift pump to circulate said liquid medium through said trough, said pump comprising a substantially vertical stand pipe having a medium inlet, a medium outlet located above said inlet and means for introducing a stream of gas bubbles into aqueous medium inside said pipe to cause said medium to rise therein and means for injecting a stream of minute gas bubbles into aqueous medium inside said pipe to increase the buoyancy of organic substances and of microalgae in said medium by adsorption of said minute gas bubbles, said inlet and outlet being connected to said trough at locations adjacent said discharge and inlet ends respectively so that circulation of said medium in said trough from said inlet end toward said discharge end is facilitated;
a source of carbon dioxide;
tubing means connected between said means for injecting a stream of minute bubbles and said source of carbon dioxide, for directing a flow of carbon dioxide from said source into said liquid medium;
skimming means for skimming off organic substances raised to the surface of said medium due to adsorption onto minute bubbles in said stand pipe;
harvesting means for skimming off microalgae raised to the surface of said medium;
a container comprising two substantially transparent panels which are closely spaced and joined together to define a water tight compartment therebetween, said container being positioned such that sunlight passes through said panels and subsequently strikes said medium circulating through said trough;
an aqueous $CuSO_4$ solution contained in said compartment to serve as a filter which adsorbs infrared and ultraviolet radiation of said light;
mixing means for causing said medium to travel through said trough in a vortical path so that individual algal cells are alternately positioned in portions of said medium distant and adjacent to said light source and thus are alternately exposed to maximum intensity light when in said adjacent portion and decreasing light intensity at progressively more distant portions;
means for maintaining the temperature of said aqueous medium within a range conducive to the growth and reproduction of said algal species;
means for extracting heat energy from said $CuSO_4$ solution; and
means for replenishing nutrient salts in said medium as they are consumed by said mocroalgae so that sufficient nutrients are maintained to sustain desired algal growth and reproduction rates.

15. A continuous process for mass culture of a selected species of marine microalgae comprising:
filling an algal culture container with a liquid culture medium precursor comprising sea water in which is dissolved a mixture of nutrient salts which, in grams per 100 liters of sea water, consists essentially of 50.7 g. $HNO_3$, 7.8 g. $H_3PO_4$, 4.3 g. KCl. 1.86 g. $Na_2EDTA$, 0.020 g. $FeCl_3.6H_2O$, 0.00368 g. $(NH_4)_6Mo_7O_{24}.4H_2O$, 0.00105 g. $H_3BO_3$, 0.00040 g. $ZnCl_2$, and lesser amounts of both $CuCl_2.2H_2O$ and $MnCl_2.4H_2O$;
adding an amount of KOH to said precursor sufficient to adjust its pH to a level which facilitates a desired reproduction and growth pattern for a selected marine algal species and to complete said precursor's nutrient content whereby a liquid medium suitable for the growth of said marine algal species is formed;
innoculating said medium with a culture of said algal species;
circulating said innoculated medium through an open trough at an average depth of between 0.5 and 5.0 cm. by withdrawing medium from one end of the trough and replacing it in the other end;
maintaining the temperature of said innoculated medium within a range conducive to the growth and reproduction of said algal species;
channeling the flow of innoculated medium from said one end of said trough through the vertical stand pipe of a gas lift pump mechanism equipped for the injection of minute gas bubbles into liquid medium passing therethrough to:
 a. accomplish said circulating; and
 b. bring organic substances and the cells of said algal culture into contact with a stream of minute gas bubbles which are adsorbed thereon to increase the buoyancy of said organic substances and said microalgae so that they tend to rise to the surface of medium in the trough;
moving liquid medium containing dissolved organic substances and algal cells with adsorbed minute gas bubbles through said trough at a rate such that the relatively small and light organic substances with adsorbed gas bubbles rise to the surface of said medium and the relatively large and heavier algal cells with adsorbed gas bubbles are carried by the current and not allowed to rise to said surface;
skimming said organic substances from said surface;
subsequently slowing the rate at which said liquid medium moves through said trough so that algal cells with adsorbed gas bubbles rise to said surface;
skimming algal cells from said surface;
exposing the surface of medium in the trough to sunlight which has been filtered by passage through a thin layer of an aqueous solution consisting essentially of water in which is dissolved an amount of $CuSO_4.5H_2O$ sufficient to facilitate the photosynthesis of the microalgae by removing at least ninety-nine percent of all radiation below 350 nanometers and above 700 nanometers from the incident sunlight;

alternately positioning individual cells of the algae in portions of said medium distant and adjacent to said medium surface and thus alternately exposing the cells to maximum light intensity when adjacent to said surface and decreasing light intensity when progressively more distant from said surface;

replenishing nutrient salts in the medium as they are consumed by said microalgae so that sufficient nutrients are maintained in said medium to sustain desired algal growth and reproduction rates; and injecting into said medium at least 235 g. of $CO_2$ per 100 liters of medium per day.

* * * * *